US009453195B2

(12) United States Patent
Fairbrother et al.

(10) Patent No.: US 9,453,195 B2
(45) Date of Patent: Sep. 27, 2016

(54) **NON-PATHOGENIC F18 *E. COLI* STRAIN AND USE THEREOF**

(71) Applicant: Prevtec Microbia Inc., Montréal (CA)

(72) Inventors: John Morris Fairbrother, Saint-Hyacinthe (CA); Éric Nadeau, Otterburn Park (CA); Clarisse Desautels, Saint-Hyacinthe (CA)

(73) Assignee: PREVTEC MICROBIA INC., Montreal, Quebec (CA)

( * ) Notice: Subject to any disclaimer, the term of this patent is extended or adjusted under 35 U.S.C. 154(b) by 0 days.

(21) Appl. No.: 14/414,964

(22) PCT Filed: Jul. 18, 2013

(86) PCT No.: PCT/CA2013/000660
§ 371 (c)(1),
(2) Date: Jan. 15, 2015

(87) PCT Pub. No.: WO2014/012172
PCT Pub. Date: Jan. 23, 2014

(65) Prior Publication Data
US 2015/0152377 A1    Jun. 4, 2015

Related U.S. Application Data

(60) Provisional application No. 61/674,179, filed on Jul. 20, 2012.

(51) Int. Cl.
| | | |
|---|---|---|
| *A01N 63/00* | (2006.01) | |
| *C12N 1/20* | (2006.01) | |
| *A61K 35/74* | (2015.01) | |
| *C12R 1/19* | (2006.01) | |

(52) U.S. Cl.
CPC ............. *C12N 1/20* (2013.01); *A61K 35/74* (2013.01); *C12R 1/19* (2013.01)

(58) Field of Classification Search
None
See application file for complete search history.

(56) References Cited

U.S. PATENT DOCUMENTS

| | | |
|---|---|---|
| 6,355,859 B1 | 3/2002 | Bosworth |
| 7,163,820 B1 | 1/2007 | Nagy et al. |
| 7,371,558 B2 | 5/2008 | Cervin |
| 7,981,411 B2 | 7/2011 | Nadeau et al. |
| 2011/0318379 A1 | 12/2011 | Francis et al. |

FOREIGN PATENT DOCUMENTS

WO        02/43649 A2    6/2002

OTHER PUBLICATIONS

Riley et al., Nuc. Acid Res., 34(1):1-9 (2006).*
Invivogen product information (2011).*
Solomon et al., App. Env. Microbiol., 68(1):397-400 (2002).*
Kim et al., Can. J. Vet. Res., 74:59-64 (2010).*
Barth, S., et al., "Virulence and Fitness Gene Patterns of Shiga Toxin-Encoding *Escherichia coli* Isolated From Pigs With Edema Disease or Diarrhea in Germany," Berliner and Münchener Tierärztliche Wochenschrift 120(7-8):307-316, Jul.-Aug. 2007.
Debroy, C., et al., "Comparison of Genotypes of *Escherichia coli* Strains Carrying F18ab and F18ac Fimbriae From Pigs," Journal of Veterinary Diagnostic Investigation 21(3):359-364, May 2009.
Deshpande, M.V., "Ethanol Production From Cellulose by Coupled Saccharification/Fermentation Using Saccharomyces cerevisiae and Cellulase Complex From Sclerotium rolfsii UV-8 Mutant," Applied Biochemistry and Biotechnology 36(3):227-234, Sep. 1992.
Fairbrother, J.M., et al., "*Escherichia coli* in Postweaning Diarrhea in Pigs: An Update on Bacterial Types, Pathogenesis, and Prevention Strategies," Animal Health Research Reviews 6(1):17-39, Jun. 2005.
International Search Report mailed Oct. 7,2013, issued in corresponding International Application No. PCT/CA2013/000660, filed Jul. 18, 2013, 3 pages.
MacLeod, D.L., et al., "Reproduction of Edema Disease of Swine With Purified Shiga-Like Toxin-II Variant," Veterinary Pathology 28(1):66-73, Jan. 1991.
Nagy, B., et al., "Biological Relationship Between F18ab and F18ac Fimbriae of Enterotoxigenic and Verotoxigenic *Escherichia coli* From Weaned Pigs With Oedema Disease or Diarrhoea," Microbial Pathogenesis 22(1):1-11, Jan. 1997.
Niewerth, U., et al., "The AIDA Autotransporter System Is Associated With F18 and Stx2e in *Escherichia coli* Isolates From Pigs Diagnosed With Edema Disease and Postweaning Diarrhea," Clinical and Diagnostic Laboratory Immunology 8(1):143-149, Jan. 2001.
Vögeli, P., et al., "Genes Specifying Receptors for F18 Fimbriated *Escherichia coli*, Causing Oedema Disease and Postweaning Diarrhoea in Pigs, Map to Chromosome 6," Animal Genetics 27(5):321-328, Oct. 1996.
Waddell, T.E., et al., "Interaction of Verotoxin 2e With Pig Intestine," Infection and Immunity 64(5):1714-1719, May 1996.
Extended European Search Report mailed Dec. 15, 2015, issued in corresponding European Application No. EP 13819873, filed Jul. 18, 2013, 9 pages.
Bertschinger, H.U., et al., "Active Oral Immunization of Suckling Piglets to Prevent Colonization After Weaning by Enterotoxigenic *Escherichia coli* with Fibriae F18,"Veterinary Microbiology 71(3/04):255-267, Feb. 2000.
Bianchi, A.T.J., et al., "Parental Vaccination of Mice and Piglets with F4+ *Escherichia coli* Suppresses the Enteric Anti-F4 Response Upon Oral Infection," Vaccine 14(3):199-206, Feb. 1996.
Bozic, F., et al., "Adjuvant Activity of Levamisole for Experimental F18ac+ *Escherichia coli* Oral Vaccine Against 3orcine Post-Weaning Colibacillosis," Veterinarski Arhiv 81(2):199-209 Jan. 2011.
Luo, U., et al., "F4(+) ETEC Infection and Oral Immunization with F4 Fimbriae Elicits an IL-17-Dominated Immune Response," Veterinary Research 46(1):1-14, 2015.
Verdonck, F., et al., "The Polymeric Stability of the *Escherichia coli* F4 (K88) Fimbriae Enhances its Mucosal Immunogenicity Following Oral Immunization," Vaccine 26(45):5728-5735, Oct. 2008.

\* cited by examiner

*Primary Examiner* — Thomas J Visone
(74) *Attorney, Agent, or Firm* — Christensen O'Connor Johnson Kindness PLLC

(57) ABSTRACT

There is provided an isolated *E. coli* strain deposited at the International Depositary Authority of Canada (IDAC) on Jun. 20, 2013 and attributed accession number 200613-01. There is also provided methods of using this strain for preventing edema disease or diarrhea caused by an F18 pathogenic *E. coli* infection in an animal.

18 Claims, 3 Drawing Sheets

NON-PATHOGENIC F18 *E. COLI* STRAIN AND USE THEREOF

CROSS-REFERENCE TO RELATED APPLICATION

This application claims the benefit of U.S. Provisional Application 61/674,179, filed Jul. 20, 2012, the contents of which are incorporated herein by reference in their entirety.

TECHNICAL FIELD

This application relates to a non-pathogenic F18 *E. coli* strain and to the use thereof.

BACKGROUND

Edema disease and diarrhea typically are common diseases amongst animals raised by breeders. For example, edema disease in weaned piglets is typically caused by shiga toxin-encoding *Escherichia coli* (STEC) strains encoding the Shiga toxin type 2e (Stx2e) (MacLeod et al., 1991, Vet Pathol 28:66-73), while secretory diarrhea in newborn and weaned piglets is typically caused by enterotoxigenic *Escherichia coli* strains (ETEC) encoding for heat stable (STa, STb, EAST1) and/or heat labile (LT) enterotoxins (Gyles and Fairbrother, 2010, Escherichia coll. In: Pathogenesis of bacterial infections in animals, ed. Gyles C L, Prescott J F, Songer G, Thoen C O, 4th ed., pp 267-308. Blackwell Publishing, Ames, Iowa; Nagy et al., 1997, Microb Pathog 22:1-11). Some pathogenic strains express both the Stx2e genes and enterotoxin genes and therefore may be capable of causing symptoms of edema disease and those of diarrhea in the same animal (STEC/ETEC) (Barth et al., 2007, Berl Munch Tierarztl Wochenschr 120:307-316).

A deficiency associated with many conventional therapeutic or prophylactic compositions and methods for intestinal bacterial infections associated with symptoms of edema disease and/or diarrhea disease is their low reliability or efficacy. There is therefore a need for an improved therapeutic or prophylactic compositions and methods for edema disease and/or diarrhea disease.

SUMMARY

In one non-limiting broad aspect there is provided an isolated *Escherichia coli* strain deposited at the International Depositary Authority of Canada (IDAC) on Jun. 20, 2013 and attributed accession number 200613-01. The address for the IDAC is 1015 Arlington Street Winnipeg, Canada R3E 3R2.

In another non-limiting broad aspect there is provided a method for preventing a pathogenic F18 *Escherichia coli* (*E. coli*) intestinal infection in an animal, comprising intestinal delivery to the animal of an effective amount of a live *E. coli* strain deposited at the International Depositary Authority of Canada (IDAC) on Jun. 20, 2013 and attributed accession number 200613-01. The address for the IDAC is 1015 Arlington Street Winnipeg, Canada R 3E 3R2.

In another non-limiting broad aspect there is provided a method for preventing edema disease or diarrhea caused by a pathogenic F18 *Escherichia coli* (*E. coli*) infection in an animal, comprising intestinal delivery to the animal of an effective amount of a live *E. coli* strain deposited at the International Depositary Authority of Canada (IDAC) on Jun. 20, 2013 and attributed accession number 200613-01.

In one non-limiting embodiment, the live *E. coli* strain is in a lyophilized form. In another non-limiting embodiment, the live *E. coli* strain is in association with a feed acceptable carrier, for example the live *E. coli* strain may be diluted, incorporated into, or suspended in the feed acceptable carrier. In another non-limiting embodiment, the live *E. coli* strain is in frozen form.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

A detailed description of the embodiments of the present invention is provided herein below with reference to the accompanying drawings in which.

DETAILED DESCRIPTION OF EMBODIMENTS

Figure 1:
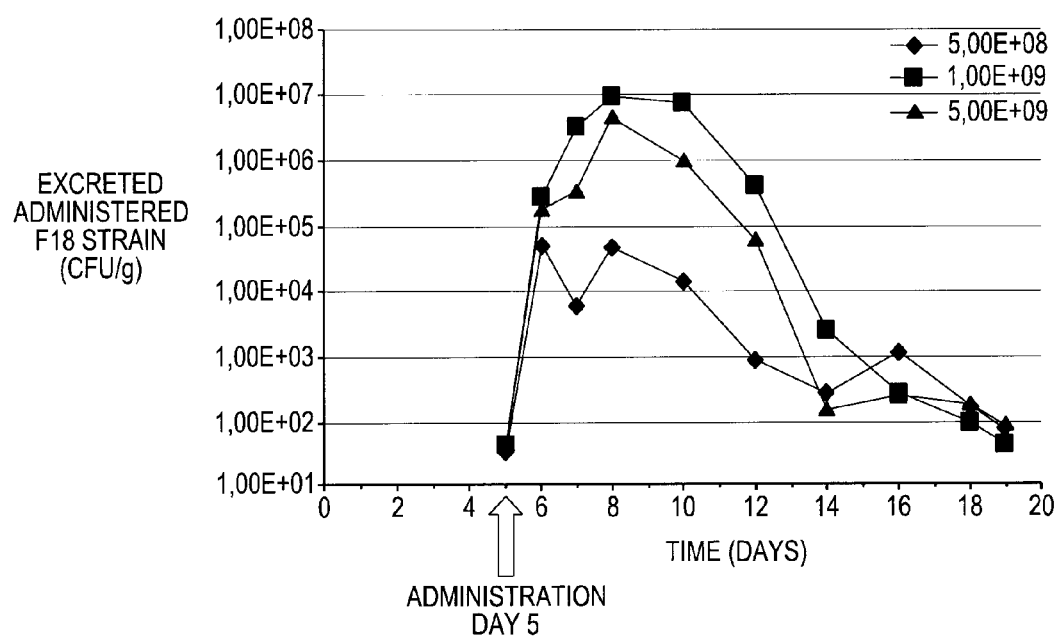
FIG. 1: Is a non-limiting graphic that illustrates fecal excretion of the non-pathogenic F18 strain after administration of the live non-pathogenic F18 strain according to variable dosages, shown as the inverse log of the average of logarithmic colony forming units (CFU).

Generally, porcine STEC and many porcine ETEC strains express the F18 determinant. The F18 determinant is a fimbriae that facilitates bacterial colonization of the mucosal surface of the intestine (Fairbrother et al. 2006, Postweaning *Escherichia coli* diarrhea and edema disease. In: Diseases of swine, ed. Straw B, Zimmermann J J, D'Allaire S, Taylor D J, 9th ed., pp. 649-662. Blackwell Publishing, Ames, Iowa). It is believed that F18 fimbriae mediate adhesion of an F18 expressing bacterial cell to an enterocyte receptor, the ECF18R receptor, which is exposed by the enterocytes of the small intestine on their apical cytoplasmic membrane (Vögeli et al. 1996, Anim Genet 27:321-328; Waddell et al. 1996, Infect Immun 64:1714-1719).

Some porcine STEC and STEC/ETEC strains can express other cytoadhesive fimbriae or nonfimbrial adhesins in addition to the F18 fimbria, in particular F4 or F5 fimbriae or the "adhesin involved in diffuse adherence" (AIDA) (Barth et al., 2007, Berl Munch Tierarztl Wochenschr 120:307-316; DebRoy et al. 2009, J Vet Diagn Invest 21:359-364; Fairbrother et al., supra; Niewerth et al.: 2001, Clin Diagn Lab Immunol 8:143-149). While the AIDA adhesin occurs frequently in both pathogens, F4 or F5 fimbriae are rare in those strains.

On farm, post-weaning diarrhea (PWD) and edema disease (ED) in swine generally occur in the first 2 weeks post-weaning and are associated with infection by pathogenic F4 or F18 enterotoxigenic *E. coli* (ETEC) strains for PWD and by pathogenic F18 Shiga toxin producing *E. coli*

(STEC) strains for ED. For both strains, the fimbriae (i.e., F4 or F18) allow adhesion of the bacteria to their specific receptors, located on small intestinal villi, followed by division of the bacteria and colonization of the intestine.

In PWD, F4 receptors are expressed in about 30 to 40% of pigs and F18 receptors are detected in about 70 to 80% of pigs. The pathogen strains produce a combination of several toxins such as LT, STa and STb. Pigs infected with ETEC-F4 generally show very high morbidity, delay in growth, watery and projectile diarrhea which often lead to the infected animal's death.

For ED, the F18 receptors are detected in about 70 to 80% of pigs. The toxin associated to STEC is Stx2e, a vasotoxin that acts on vascular endothelial cells resulting in edema and subsequent neurological signs including ataxia, decumbency and eventually, as for PWD, often lead to the infected animal's death.

As used herein, the expression "F18 *E. coli*" or "F18 strain" relates to an *E. coli* strain that expresses the F18 determinant (fimbriae).

As used herein, the expression "F4 *E. coli*" or "F4 strain" relates to an *E. coli* strain that expresses the F4 determinant (fimbriae).

The person of skill will recognize that the herein described non-pathogenic F18 strain may be manipulated so as to obtain a mutant or variant strain thereof, a strain that has all the identifying characteristics of the strain described herein, without undue effort. Methods of creating mutants or variants are common and well known in the art. For example, U.S. Pat. No. 7,371,558 (which is herein incorporated by reference in its entirety) discloses a summary of some methods for creating a "mutant or variant thereof." Specific methods for creating mutants using radiation or chemical agents are also well documented in the art. See, for example, Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol. 36, 227 (1992). A mutant or variant strain thereof may also be identified as having a genome or significant part thereof that hybridizes under conditions of high stringency to the genome of the strain described herein. The person of skill will be able to recognize how significant a part of a genome must be so as to consider whether a given strain is a "mutant or variant thereof." As such, the person of skill will reasonably expect that the present invention may be practiced using such variant or mutant thereof, without undue effort.

As used herein, the expression "effective amount" relates to an amount that will elicit the desired biological response of a tissue, system or animal. Such an effective amount of the herein described live F18 *E. coli* strain can be, for example, but without being limited thereto, the amount that is sufficient for preventing intestinal bacterial infection, minimizing bacterial excretion, preventing a disease caused by intestinal bacterial infection, and the like. The effective amount to be used may vary according to a number of factors. For instance, the number of factors may be selected from the type of animal, initial weight of the animal, growth phase of the animal, environment, feed acceptable carrier associated with the live strain, i.e., animal facilities, type and management of production, hygienic status of the facilities, the animal's stress after weaning or hatching, feed and supplements used, health of the animal and concomitant diseases or treatment, and the like. For example, the effective amount can be, but without being limited thereto, any amount selected within the range of about $5 \times 10^6$ to about $3 \times 10^{10}$ CFU. The person skilled in the art will be able to determine a suitable effective amount without undue effort.

As used herein, the term "animal" refers to any young or adult animal suitable to be used in accordance with the present invention. In one non-limiting embodiment, the term "animal" refers to a swine. In one non-limiting embodiment, the term "animal" refers to a pig. In one non-limiting embodiment, the pig is a pre-weaned pig. In another non-limiting embodiment, the pig is a post-weaned pig. The person skilled in the art will be able to determine a suitable animal without undue effort.

As used herein, the term "intestinal delivery" refers to a mode of administration that enables the strain to eventually reach the gastrointestinal tract, and more preferably the intestines. In one non-limiting embodiment, the intestinal delivery is performed by oral administration of the strain. In another non-limiting embodiment, the intestinal delivery is performed by rectal administration, for example via a suppository. The person skilled in the art will be able to determine a suitable mode of administration without undue effort.

As used herein, the expression "feed acceptable carrier" refers to any carrier, diluent or excipient that is compatible with the herein described strain and can be given to an animal without adverse effects. Suitable feed acceptable carriers known in the art include, but are not limited to, water, saline, glucose, dextrose, buffered solutions, and the like. Such a carrier is advantageously non-toxic to the strain and not harmful to the animal. It may also be biodegradable. The carrier may be a solid or liquid feed acceptable carrier. A suitable solid feed acceptable carrier is a non-toxic ingestable carrier. For instance, this solid feed acceptable carrier may be a common solid feedstuff such as the component of a typical animal diet consisting of cereal products, such as barley meal, maize meal or wheat feed, nut and seed products, such as decorticated ground nut cake or cotton seed cake, or extracted cotton seed cake, together with minor amounts of, for example, feather meal, seaweed meal, bone meal, bone flour, chalk, salt, urea and vitamins; or it may be an inert solid diluent or carrier of no nutritional value, for example kaolin, talc, calcium carbonate, fuller's earth, attapulgus clay, ground oyster shells or ground limestone; or it may be starch or lactose. In another specific implementation, the solid feed acceptable carrier may be ground corn, soybean meal, whey, animal fat, and the like. A suitable liquid feed acceptable carrier is, for example, water and preferably drinking water; milk such as whole or skim milk; or a culture medium such as a trypsone soy broth (TSB). The person skilled in the art will be able to determine a suitable feed acceptable carrier without undue effort.

The scope of the claims should not be limited by the preferred embodiments set forth in the following examples, but should be given the broadest interpretation consistent with the description as a whole.

EXAMPLES

Example 1 a) Non-Pathogenic F18 *E. coli* Strain

The *E. coli* strain deposited at the International Depositary Authority of Canada (IDAC) on Jun. 20, 2013 and attributed accession number 200613-01 was isolated from feces of a pig in 1996 at the OIE reference laboratory for *Escherichia coli* (EcL) at the Faculté de medicine vétérinaire (FMV), Université de Montréal (UdeM), Saint-Hyacinthe, Quebec, Canada by Dr. J. M. Fairbrother.

An identification of the strain was done using the API system. The API 20E code for Master Seed is 5004552. Serotyping of the strain revealed a serotype of O141:K94: H-.

Virotyping of the strain was done by colony hybridization and/or polymerase chain reaction (PCR). Virotyping results showed that the strain was positive for F18 and AIDA whereas it was negative for the following toxins: STa, STb, LT, EAST1, Stx1, Stx2, CNF, F4, F5, F6, F17, F41, P, AFA, Eae, Paa, Tsh, Aerobactin genes. This strain is thus a non-pathogenic *E. coli* strain.

The strain is resistant to the following antimicrobials: amoxicillin, ampicillin, clindamycin, doxycycline, erythromycin, neomycin, penicillin, spectinomycin, streptomycin, sulfachlorpyridazin, sulfadimethoxin, sulfathiazole, tiamulin, tilmicosin, tetracycline (chlor and oxy) and tylosin, while being sensitive to the following antimicrobials: apramycin, ceftiofur, colistine, danofloxacin, enrofloxacin, and gentamicin.

b) Non-Pathogenic F4 *E. coli* Strain

A non-pathogenic F4 *E. coli* strain may also be used in combination with the non-pathogenic F18 strain herein described. In one non-limiting embodiment, the non-pathogenic F4 *E. coli* strain is any non-pathogenic strain that expresses the F4 determinant. In one non-limiting embodiment, the non-pathogenic F4 *E. coli* strain is a recombinant strain, for example the pMK005 strain (Kehoe et al., J Bacteriol. 1983 September; 155(3):1071-7). In another non-limiting embodiment, the non-pathogenic F4 *E. coli* strain is a natural strain, for example the strain deposited at the International Depositary Authority of Canada on Jan. 21, 2005 and attributed accession number IDAC 210105-01, as described in U.S. Pat. No. 7,981,411 (the entire contents thereof are herein incorporated by reference in their entirety).

Example 2

In a broad aspect, the purpose of this study was to evaluate the impact of different oral doses of the herein described non-pathogenic F18 strain on fecal excretion thereof and on anti-F18 systemic humoral responses.

The following Table 1 summarizes generally the study schedule:

| Day | Event |
| --- | --- |
| 0 | Arrival of pigs in the experimental unit and distribution into 3 groups |
| 0-5 | Acclimatization period |
| 2 and 5 to 19 | Fecal sampling for PCR |
| 5 | Vaccination |
| 5 to 8, 10, 12, 14, 16, 18 and 19 | Fecal sampling for viable count of vaccine strain (based on hemolytic colonies) |
| 5, 10, 12, 15 and 19 | Blood sample |
| 8 | First necropsy |
| 19 | Final necropsy and end of experiment |

I—Study Design
a) Animals

Blood samples of 50 nursing piglets were taken for F18 receptor status detection analysis and piglets were ear tagged. Selected weaned pigs (males and females), aged between 17 and 20 days, were purchased from a local farm located in the Montérégie, Québec, Canada. Animals were transported to the isolation facilities. The farm selected showed no recent (less than 6 months) Porcine Reproductive and Respiratory Syndrome (PRRS) and post-weaning disease episodes. The pigs were healthy pigs and weighted between 4 to 6 Kg. A total of twenty one (21) pigs, positive for F18-receptor status, were used, randomly separated using ear tag numbers in three (3) groups of 7 animals (three different F18 composition doses). At day 2 post-weaning, a fecal sample was taken to determine the existing colonisation with F4 positive and F18 positive strains using PCR. No animal was found to be positive for either F4 positive or F18 positive bacteria at day 2 post-weaning.

b) Housing and Feeding

Treatment groups were held in separate rooms. Animals had ad libitum access to water and were fed twice daily during the study. The animals diet was constituted of a high soybean meal as described in U.S. Pat. No. 6,355,859 (the entire content thereof is herein incorporated by reference in its entirety). No concurrent medication or vaccination was administered during the study.

c) Strain Preparation and Administration

Two growth curves were prepared the same way to evaluate the time required by the non-pathogenic F18 strain to attain its optimal yield. Working Seed (WS) was used to prepare the growth curve and the culture that was used for preparing the F18 composition. One milliliter of the WS was used to inoculate 500 mL of TrypticSoy Broth without materials of animal origin. The culture was incubated approximately 6.5 hours at 37° C. with agitation (180 rpm). A viable count was done to evaluate the yield of the F18 strain culture and a PCR reaction was used to demonstrate that the appropriate strain was used during the assay. Based on the results, the culture was adjusted to meet the doses to be tested using sterile TSB without materials of animal origin: Group 1, $5 \times 10^8$ CFU/dose; Group 2, $1 \times 10^9$ CFU/dose; and Group 3, $5 \times 10^9$ CFU/dose.

Nine (9) doses of non-pathogenic F18 strain composition were prepared for each formulation, 2 more than the number of piglets to be treated to compensate for any composition loss. Six (6) mL of F18 composition were administered orally to every piglet. The F18-composition was administered at day 5 post-weaning using an esophageal tube.

II—Observations and Evaluation
a) General Health

Piglets were observed twice daily for general health: behavior, dehydration, appetite, and general physical condition. Mobility and hair aspect were also evaluated.

b) Diarrhea

Fecal consistency are scored daily as follow: 0, normal; 1, pasty; 2, presence of liquid but more solid particles than liquid; 3, presence of more liquid than solid particles; and 4, totally liquid.

c) Excretion of the Administered Non-Pathogenic F18 Strain

At day 2 and days 5 to 19 post-weaning, feces were tested by PCR (multiplex: LT, STa, STb and F4; F18, Stx2e and AIDA) following enrichment in Luria-Bertoni (LB) broth to evaluate the presence of the administered non-pathogenic F18 strain in each group. A sample positive for F18 was considered positive for the administered non-pathogenic F18 strain. At days 5 to 8, 10, 12, 14, 16, 18 and 19 post-weaning, a viable count was done on feces samples using Tryptic Soy Agar II (TSA II)—5% sheep blood to evaluate the level of the administered non-pathogenic F18 strain excreted after administration. Only haemolytic colonies with typical *E. coli* morphology were counted.

d) Immunization Evaluation

Blood samples were collected at days 5, 10, 12, 15 and 19 post-weaning to evaluate by ELISA the optimal immune response accordingly to the dosage of the administered non-pathogenic F18 strain.

III—Necropsy a) Necropsy

A first necropsy was conducted 3 days post-vaccination, at day 8 post-weaning on 2 animals chosen randomly, and gross abnormalities are evaluated. The second necropsy was conducted at the end of the study, thus on day 19 post-weaning, which was 14 days post-vaccination on all the remaining animals.

b) Intestinal Content Consistency

Intestinal content consistency are scored in the jejunum, ileum, caecum, colon and rectum as follow: 0, normal; 1, pasty; 2, presence of liquid but more solid particles than liquid; 3, presence of more liquid than solid particles or totally liquid.

c) Colonization of the Ileum by the Vaccine Strain

A 2 centimeters portion of the ileum was sampled at 10 cm proximal of the ileocaecal junction. Live bacterial enumeration was performed using TSA II—5% sheep blood, where only haemolytic colonies with typical *E. coli* morphology were counted.

IV—Results

No mortality was observed in both treated and control animals throughout the study. All pigs selected were positive for F18 receptor as per the PCR-RFLP method. In general, piglets were in good health all along the study. Few animals showed reduced mobility that appeared before administration of the non-pathogenic F18 strain or due to injuries thus not related to the administration of the non-pathogenic F18.

During this study, a score of 2 or more was considered as diarrhea. On the 21 animals, 5 showed transient mild diarrhea after F18 administration. One animal (pig 5 in group 3) had diarrhea (score of 3) for 2 consecutive days (Tables 2a, 2b and 2c).

Fecal samples were tested daily by PCR to detect presence of the F18 administered strain; 3 animals in group 2 ($1\times10^9$ CFU/dose) were positive for the F18 administered strain, at the latest, on day 11 post-vaccination, where group 3 ($5\times10^9$ CFU/dose) had 1 piglet positive at day 10, 1 at day 8 and 3 at day 7 post-vaccination. For group 1 ($5\times10^8$ CFU/dose) 1 piglet was positive for the non-pathogenic F18 administered strain at day 8 post-vaccination, 1 piglet at day 7 and 2 at day 6 post-vaccination (Tables 2a, 2b and 2c).

TABLE 2a

Scores, duration and severity of diarrhea for group administered with $5 \times 10^8$ CFU/dose

| ID | \*2 0 | 1 | 2 | 3 | 4 | 5 | 6 | 7 | 8 | 9 | 10 | 11 | 12 |
|---|---|---|---|---|---|---|---|---|---|---|---|---|---|
| 9  | 0 | 0 | ND | ND | ND | 1 | 0 | 0 | 2 | D | D | D | D |
| 18 | 0 | 0 | ND | ND | ND | 0 | 0 | 0 | 0 | 0 | 0 | 0 | 1 |
| 23 | 0 | 0 | ND | ND | ND | 0 | 0 | 1 | 1 | 0 | 0 | 0 | 0 |
| 27 | 0 | 0 | ND | ND | ND | 0 | 0 | 0 | 0 | 0 | 1 | 1 | 0 |
| 30 | 0 | 0 | ND | ND | ND | 0 | 0 | 0 | 0 | D | D | D | D |
| 33 | 0 | 0 | ND | ND | ND | 0 | 0 | 0 | 0 | 0 | 0 | 0 | 0 |
| 50 | 0 | 0 | ND | ND | ND | 0 | 0 | 0 | 0 | 0 | 0 | 0 | 0 |
| MD\*5 | 0 | 0 |  |  |  | 0 | 0 | 0 | 0 | 0 | 0 | 0 | 0 |

| ID | 13 | 14 | 15 | 16 | 17 | 18 | 19 | Duration\*3 Max = 14 | Severity\*4 Max = 56 |
|---|---|---|---|---|---|---|---|---|---|
| 9  | D | D | D | D | D | D | D | 1 | 2 |
| 18 | 0 | 0 | 1 | 0 | 1 | 0 | 0 | 0 | 3 |
| 23 | 0 | ND | 0 | 0 | 0 | 0 | 0 | 0 | 2 |
| 27 | 0 | 0 | 0 | 0 | 0 | 1 | 0 | 0 | 3 |
| 30 | D | D | D | D | D | D | D | 0 | 0 |
| 33 | 0 | 0 | 0 | 0 | 0 | 1 | 0 | 0 | 1 |
| 50 | 0 | 0 | 0 | 0 | 0 | 0 | 0 | 0 | 0 |
| MD\*5 | 0 | 0 | 0 | 0 | 0 | 0 | 0 | 0 | 2 |

TABLE 2b

Scores, duration and severity of diarrhea for group administered with $1 \times 10^9$ CFU/dose

| ID | 0 | 1 | 2 | 3 | 4 | 5 | 6 | 7 | 8 | 9 | 10 | 11 | 12 |
|---|---|---|---|---|---|---|---|---|---|---|---|---|---|
| 6  | 0 | 0 | ND | ND | ND | 2 | 0 | 0 | 0 | 0 | 1 | 0 | 0 |
| 26 | 0 | 0 | ND | ND | ND | 0 | 0 | 0 | 0 | 0 | 0 | 0 | 0 |
| 29 | 0 | 0 | ND | ND | ND | 0 | 0 | 0 | 0 | 0 | 0 | 0 | 1 |
| 34 | 0 | 0 | ND | ND | ND | 0 | 0 | 0 | 0 | D | D | D | D |
| 37 | 0 | 0 | ND | ND | ND | 0 | 1 | 3 | 1 | D | D | D | D |
| 42 | 0 | 0 | ND | ND | ND | 0 | 0 | 0 | 0 | 0 | 0 | 0 | 1 |
| 45 | 0 | 0 | ND | ND | ND | 2 | 2 | 1 | 0 | 0 | 2 | 0 | 1 |
| MD\*5 | 0 | 0 |  |  |  | 0 | 0 | 0 | 0 | 0 | 0 | 0 | 1 |

TABLE 2b-continued

Scores, duration and severity of diarrhea for
group administered with $1 \times 10^9$ CFU/dose

| | Diarrhea score*1 at day*2 | | | | | | | Duration*3 | Severity*4 |
|---|---|---|---|---|---|---|---|---|---|
| ID | 13 | 14 | 15 | 16 | 17 | 18 | 19 | Max = 14 | Max = 56 |
| 6 | 1 | 0 | 1 | 1 | 0 | 1 | 0 | 0 | 5 |
| 26 | 0 | 0 | 0 | 0 | 0 | 0 | 0 | 0 | 0 |
| 29 | 0 | 0 | 0 | 0 | 0 | 0 | 0 | 0 | 1 |
| 34 | D | D | D | D | D | D | D | 0 | 0 |
| 37 | D | D | D | D | D | D | D | 1 | 5 |
| 42 | 0 | 0 | 0 | 0 | 0 | 0 | 0 | 0 | 1 |
| 45 | 0 | 0 | 0 | 0 | 0 | 0 | 0 | 2 | 6 |
| MD*5 | 0 | 0 | 0 | 0 | 0 | 0 | 0 | 0 | 1 |

TABLE 2c

Scores, duration and severity of diarrhea for group administered with $5 \times 10^9$ CFU/dose

| | Diarrhea score*1 at day*2 | | | | | | | | | | | | | |
|---|---|---|---|---|---|---|---|---|---|---|---|---|---|---|
| ID | 0 | 1 | 2 | 3 | 4 | 5 | 6 | 7 | 8 | 9 | 10 | 11 | 12 | 13 |
| 4 | 0 | 0 | ND | ND | ND | 0 | 0 | E | 0 | 1 | 0 | 0 | 1 | 1 |
| 5 | 0 | 0 | ND | ND | ND | 0 | 0 | 0 | 0 | 1 | 0 | 1 | 3 | 3 |
| 13 | 0 | 0 | ND | ND | ND | 0 | 0 | 0 | 0 | 0 | 0 | 1 | 0 | 2 |
| 17 | 0 | 0 | ND | ND | ND | 0 | 1 | 0 | 0 | D | D | D | D | D |
| 21 | 0 | 0 | ND | ND | ND | 0 | 0 | 0 | 0 | 0 | 0 | 0 | 0 | 0 |
| 46 | 0 | 0 | ND | ND | ND | 0 | 0 | 0 | 0 | D | D | D | D | D |
| 49 | 0 | 0 | ND | ND | ND | 0 | 1 | 0 | 0 | 0 | 0 | 0 | 0 | 0 |
| MD*5 | 0 | 0 | | | | 0 | 0 | 0 | 0 | 0 | 0 | 0 | 0 | 1 |

| | Diarrhea score*1 at day*2 | | | | | | Duration*3 | Severity*4 |
|---|---|---|---|---|---|---|---|---|
| ID | 14 | 15 | 16 | 17 | 18 | 19 | Max = 14 | Max = 56 |
| 4 | 1 | 1 | 1 | 1 | 2 | 0 | 1 | 9 |
| 5 | 0 | 2 | 1 | 1 | 1 | 1 | 3 | 14 |
| 13 | 0 | 0 | 0 | 0 | 0 | 0 | 1 | 3 |
| 17 | D | D | D | D | D | D | 0 | 1 |
| 21 | 0 | 0 | 0 | 0 | 0 | 0 | 0 | 0 |
| 46 | D | D | D | D | D | D | 0 | 0 |
| 49 | 0 | 0 | 0 | 0 | 0 | 0 | 0 | 1 |
| MD*5 | 0 | 0 | 0 | 0 | 0 | 0 | 0 | 1 |

*1Fecal consistency are scored as follows: 0, normal; 1, pasty; 2, presence of liquid but more solid particles than liquid; 3, presence of more liquid than solid particles; and 4, totally liquid;
*2Day: F18 administered strain administration;
*3Duration of diarrhea (Number of days with scores of 2 or more for the post-vaccination period; days 6 to 19);
*4Severity of diarrhea (Cumulative diarrhea scores for the post-vaccination period; days 6 to 19);
*5Median of diarrhea score.
The vertical bold line designates the last day that F18 (the vaccine strain) was detected by PCR.
ND: Not done
E: empty
D: Deceased (subjected to necropsy)

Fecal excretion of the non-pathogenic F18 administered strain was also evaluated by bacterial enumeration from fecal samples at day 5 to 8, 10, 12, 14, 16, 18 and 19. FIG. 1 shows the excretion of the strain post-administration. The level of bacteria excreted with the lower dose ($5 \times 10^8$ CFU) is inferior to the two other, the highest excretion being observed with animals from group 2, administered with a dose of $1 \times 10^9$ CFU.

No gross abnormalities were observed for internal organs. Intestinal contents consistencies were evaluated for accumulation of fluid.

In this study, a score of 2 or more was considered as fluid accumulation in an intestinal segment at day of necropsy.

Tables 3a, 3b and 3c show that one animal in group 1 presented two consecutive segments with fluid accumulation (score of 2). The other animals did not show fluid accumulation.

No undesirable event related to administration of the non-pathogenic F18 strain was observed during the study, indicating that the tested dosages were generally safe.

Based on the strain excretion evaluation, both PCR and bacteria enumeration suggested that the $1 \times 10^9$ CFU/dose is a suitable dosage for obtaining prolonged fecal excretion of this strain. Both tests demonstrated that administration of the non-pathogenic F18 strain at $1 \times 10^9$ CFU/dose was excreted on a longer period than the other tested dosages.

TABLE 3a

Intestinal content consistency scores and extent and severity of accumulation of fluid in the intestines for group administered with $5 \times 10^8$ CFU/dose

| ID | Necropsy day | Intestinal content fluid score[*1] | | | | | Extent[*2] (Max = 5) | Severity[*3] (Max = 15) |
|---|---|---|---|---|---|---|---|---|
| | | Jejunum | Ileon | Caecum | Colon | Rectum | | |
| 9  | 8  | 0 | E | 1   | 2 | 2 | 2   | 5   |
| 18 | 19 | 0 | 0 | 0   | 0 | 0 | 0   | 0   |
| 23 | 19 | 0 | 0 | 0   | 0 | 0 | 0   | 0   |
| 27 | 19 | 0 | 0 | 0   | 0 | 0 | 0   | 0   |
| 30 | 8  | 0 | E | 0   | 0 | 0 | 0   | 0   |
| 33 | 19 | 0 | 0 | 0   | 0 | 0 | 0   | 0   |
| 50 | 19 | 0 | 0 | 0   | 0 | 0 | 0   | 0   |
| MD[*4] day 8  | | 0 | E | 0.5 | 1 | 1 | 1.5 | 3.5 |
| MD[*4] day 19 | | 0 | 0 | 0   | 0 | 0 | 0   | 0   |

TABLE 3b

Intestinal content consistency scores and extent and severity of accumulation of fluid in the intestines for group administered with $1 \times 10^9$ CFU/dose

| ID | Necropsy day | Intestinal content fluid score[*1] | | | | | Extent[*2] (Max = 5) | Severity[*3] (Max = 15) |
|---|---|---|---|---|---|---|---|---|
| | | Jejunum | Ileon | Caecum | Colon | Rectum | | |
| 6  | 19 | 0 | 0 | 0 | 1 | 0 | 0 | 1 |
| 26 | 19 | 0 | 0 | 0 | 0 | 0 | 0 | 0 |
| 29 | 19 | 0 | 0 | 0 | 1 | 0 | 0 | 1 |
| 34 | 8  | 0 | 0 | 0 | 0 | 0 | 0 | 0 |
| 37 | 8  | 0 | 0 | 0 | 0 | 0 | 0 | 0 |
| 42 | 19 | 0 | E | 0 | 0 | 0 | 0 | 0 |
| 45 | 19 | 0 | E | 0 | 0 | 0 | 0 | 0 |
| MD[*4] day 8  | | 0 | 0 | 0 | 0 | 0 | 0 | 0 |
| MD[*4] day 19 | | 0 | 0 | 0 | 0 | 0 | 0 | 0 |

TABLE 3c

Intestinal content consistency scores and extent and severity of accumulation of fluid in the intestines for group administered with $5 \times 10^9$ CFU/dose

| ID | Necropsy day | Intestinal content fluid score[*1] | | | | | Extent[*2] (Max = 5) | Severity[*3] (Max = 15) |
|---|---|---|---|---|---|---|---|---|
| | | Jejunum | Ileon | Caecum | Colon | Rectum | | |
| 4  | 19 | 1 | 0 | 0 | 0 | 0 | 0 | 1 |
| 5  | 19 | 0 | 1 | 0 | 1 | 1 | 0 | 3 |
| 13 | 19 | 0 | E | 1 | 1 | 0 | 0 | 2 |
| 17 | 8  | 0 | 0 | 0 | 0 | 0 | 0 | 0 |
| 21 | 19 | 1 | E | 1 | 0 | 0 | 0 | 2 |
| 46 | 8  | 0 | 0 | 0 | 0 | 0 | 0 | 0 |
| 49 | 19 | 0 | 0 | 0 | 0 | 0 | 0 | 0 |
| MD[*4] day 8  | | 0 | 0 | 0 | 0 | 0 | 0 | 0 |
| MD[*4] day 19 | | 0 | 0 | 0 | 0 | 0 | 0 | 2 |

[*1] Intestinal content consistency are scored in the jejunum, ileum, caecum, colon, and rectum, as follows: 0, normal; 1, pasty; 2, presence of liquid but more solid particles than liquid; 3, presence of more liquid than solid particles or totally liquid.
[*2] Extent of accumulation of fluid in the intestines (Number of intestinal segments with scores of 2 or more)
[*3] Severity of diarrhea (Cumulative consistency intestinal content scores for the intestinal segments)
[*4] Median of intestinal content consistency score
ND: Not done

Example 3

In a broad aspect, the purpose of this study was to evaluate the efficacy of the combined composition, including the herein described non-pathogenic F4 and F18 E. coli strains.

The following Table 4 summarizes generally the study schedule:

| DAY | EVENT |
|---|---|
| 0 | Arrival of pigs in the experimental unit and distribution into 2 groups |
| 0 to 5 | Acclimatization period |
| 1, 12, 14, 16, 18 and 19 | Fecal sampling for PCR |
| 4, 12, 17 and 19 | Blood sample |
| 5 | Oral administration of dose or placebo |
| 12, 13 and 14 | Challenge |
| 12, 14, 16, 18 and 19 | Fecal sampling for viable count of challenge strain |
| 19 | Final necropsy and end of experiment |

I—Study Design
a) Animals

Blood samples of 50 nursing piglets were taken for F18 receptor detection analysis and piglets were ear tagged. Selected weaned pigs (males and females), aged between 17 and 21 days, were purchased from a commercial farm located in the Montérégie area, Québec, Canada. Animals were transported to the isolation facilities. The farm showed no recent (less than 6 months) Porcine Reproductive and Respiratory Syndrome (PRRS) and post-weaning disease episodes. The pigs were healthy pigs and weighted between 4 to 6 Kg.

A total of twenty (20) pigs were used, randomly separated using ear tag numbers. A randomizer software was used to randomly distribute the 20 animals in two (2) groups of 10 animals (Control and administered group). At day 1 post-weaning, a fecal sample was taken to determine the existing colonization with pathogenic F4-ETEC positive strain and F18-ETEC/STEC positive strains originating from the farm using PCR analysis. Genes targeted are STa, STb, LT, F4, Stx2 and F18. No animal positive for either F4-ETEC or F18-ETEC/STEC bacteria at day 1 post-weaning was found.

b) Housing and Feeding

Treated and control groups were held in separate rooms. Animals had ad libitum access to water and feed during the study. The animals diet was constituted of a high soybean meal as described in U.S. Pat. No. 6,355,859. No concurrent medication or vaccination was administered during the study.

c) Strain Preparation and Administration

The rehydrated combined composition was diluted to obtain a minimum of $5 \times 10^8$ CFU/strain per 6-mL dose. The placebo was constituted of 6 mL of sterile water. The combined composition and placebo were orally administered using a syringe with rubber tubing.

d) Challenge Strain (F18-STEC EcL14724) Preparation and Administration

This challenge strain was deposited at the International Depositary Authority of Canada (IDAC) on Jul. 9, 2013 and attributed accession number 090713-01.

The culture was prepared to obtain an infectious dose of $1 \times 10^{11}$ CFU per piglet. Following the administration of 10 mL of calcium carbonate 1.2% ($CaCO_3$), five (5) mL of the challenge strain were orally administered to every piglet using an esophageal tube. The challenge strain was administered during three (3) consecutive days, i.e. day 12, 13 and 14 post-weaning at a concentration of $1 \times 10^{11}$ CFU/dose every day.

e) Observations and Evaluation

Piglets were observed twice daily for general health: behaviour, appetite, general physical condition, mobility and hair aspect was evaluated. Dehydration and body temperature was observed once a day. Excretion of the challenge strain was evaluated by PCR and viable bacterial count (CFU). Blood samples were analyzed using specific Enzyme-Linked Immunosorbent assays (ELISA). Results were presented as percentage of positivity (PP %) versus the positive control.

II—Necropsy

Colonization of the ileum and the caecum by the challenge strain was determined as follows. A 2 centimeters portion of the ileum was sampled at 10 cm proximal of the ileocaecal junction as well as a portion of the caecum. Live bacterial enumeration was performed using TSA II—5% sheep blood, where only haemolytic colonies with typical E. coli morphology were counted after 12 to 18 hours incubation at 37° C.

III—Results
a) General Information

From the 50 piglets tested, 30 were susceptible to F18 strain adhesion and 20 animals were randomly selected for the trials. In general, piglets were in good health before the challenge.

The following Table 5 shows PCR results of excreted challenge strain from feces of treated and control animals:

| | Pigs (%) excreting the challenge strain at day post-last challenge (day post-weaning) | | | |
|---|---|---|---|---|
| | 0 (14) | 2 (16) | 4 (18) | 5 (19) |
| Placebo | 100% | 100% | 67% | 56% |
| Combined composition | 100% | 60% | 0% | 0% |

As demonstrated in Table 5, administration of the combined composition reduced excretion of the challenge strains compared to pigs which received a placebo. More than half of the placebo animals (56%) were still excreting the challenge strain 5 days after the last challenge (end of study) while the challenge strain was not detected in animals treated with the combined composition as early as 4 days post-last challenge.

Figure 2:
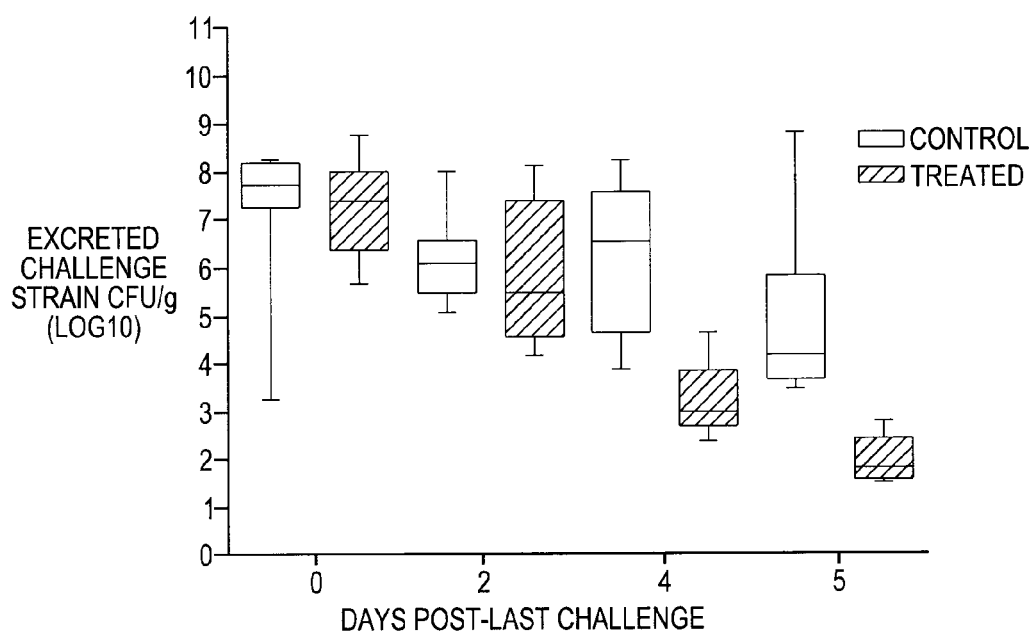
FIG. 2: Is a non-limiting graphic that illustrates fecal excretion of an F18-STEC pathogenic challenge strain: comparison between animals having been treated with the combined composition and control animals.

FIG. 2 shows viable bacterial count (CFU)/g of excreted challenge strain from feces of treated and control animals. A peak in the concentration of the excreted challenge strain is seen at post-weaning day 14 (0 day post-challenge) for both treated and control animals. In treated animals, the concentration of the challenge strain in feces started to decrease at day 2 post-last challenge (post-weaning day 16), and further reductions were observed compared to placebos at days 4 and 5 post-last challenge. These results are in accordance with the PCR results. More precisely, administration of the combined composition reduced the excretion level of the challenge strain by about 2 log at 5 days post-last challenge (end of study).

b) Ileum and Caecum Colonization by the Challenge Strain

Figure 3:
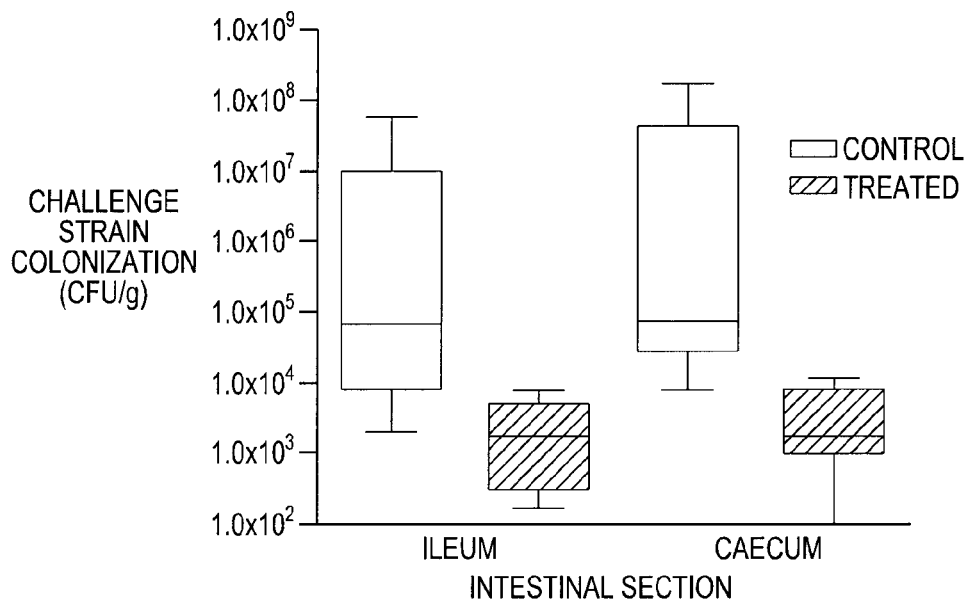
FIG. 3: Is a non-limiting graphic that illustrates colonization by the F18-STEC pathogenic challenge strain in different intestinal segments: comparison between animals having been treated with the combined composition and control animals.

Differences for intestinal colonization between the treated and placebo animals were observed for both intestinal tissue segments (ileum and caecum). FIG. 3 demonstrates that administration of the combined composition significantly reduced the colonization of the intestine by the challenge strain. More precisely, administration of the combined composition reduced the challenge strain colonization of the ileum and caecum by about 2 log at 5 days post-last challenge (end of study).

c) Immune Response Evaluation

Figure 4:
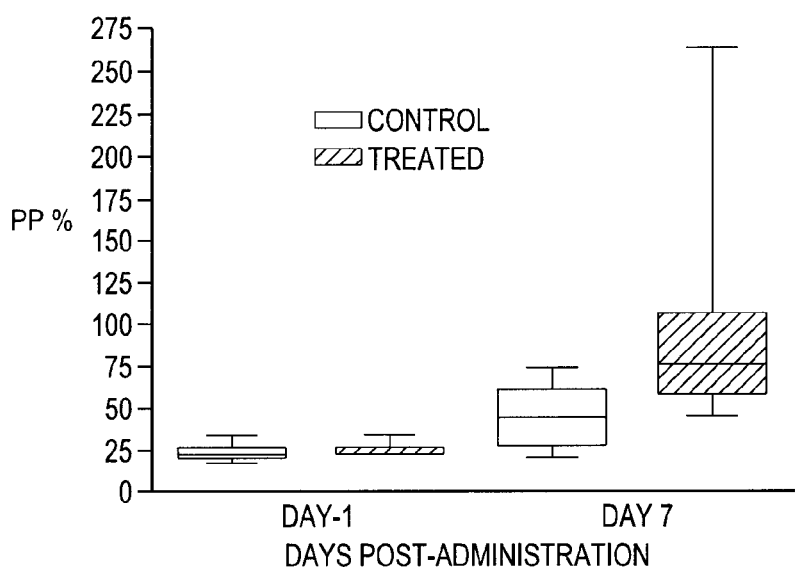
FIG. 4: Is a non-limiting graphic that illustrates immunological detection of IgM against F18 fimbriae in serological samples: comparison between animals having been treated with the combined composition and control animals.

Presence of systemic IgM against F18 fimbriae was evaluated in serum samples using specific ELISA. The combined composition treated animals showed a specific immune response as soon as 7 days post administration (FIG. 4).

Based on the resulting reduction of the challenge strain colonization, reduction of excretion and stimulation of specific anti-F18 antibodies, this study suggests that intestinal delivery of a composition including the herein described non-pathogenic F18 strain is capable of preventing F18 *E. coli* intestinal bacterial infection.

Example 4

In a broad aspect, the purpose of this study was to evaluate the efficacy of the herein described non-pathogenic F18 *E. coli* strain.

I—Study Design a) Animals

Prior to the entry of animals into the facilities, ten nursing piglets of 10 litters, for a total of 100 piglets, were sampled at the farrowing unit for DNA isolation and screened for F18 receptor (RF18+) status by a RFLP-PCR method. Thirty (30) RF18+ piglets were randomly distributed between groups by blocking by litter (1:1 ratio), with generation of block size of n=6. Piglets were allocated to one of the following groups: T1 which were administered the non-pathogenic F18 tested strain (n=15); and T2 which were administered a placebo (n=15).

Animals of the treated group (T1) were comingled into a pen of an experimental room and animals of the placebo group (T2) were comingled into a pen of another experimental room until the challenge phase. On the day of the challenge, that is 11 days after administration of the non-pathogenic F18 strain or placebo, animals of T1 (n=15) and T2 (n=15) groups were transferred, prior to challenge, into 2 separate pens located in a challenge room. All 15 pigs of a particular treatment group were commingled in the respective pen. Throughout the study, animals have ad libitum access to water, except during withholding of the water prior to vaccination. Animals are fed twice daily with non-medicated high soybean meal (U.S. Pat. No. 6,355,859).

At day 1 post-weaning, a fecal sample was taken to determine the existing colonization with pathogenic F4-ETEC positive strain and F18-ETEC/STEC positive strains originating from the farm using PCR analysis. Genes targeted are STa, STb, LT, F4, Stx2 and F18. No animal positive for either F4-ETEC or F18-ETEC/STEC bacteria at day 1 post-weaning was found. Three (3) animals of the T1 group were withdrawn from the study for animal welfare reasons. These adverse events were considered not being related to administration of the non-pathogenic F18 strain. The following Table 6 summarizes generally the animals used:

| Species: | Domestic pigs (Pen Ar Lan Naïma). This swine breed is a hybrid breed commercialized in America, Europe and Asia. |
| --- | --- |
| Number and Sex: | 30 animals; Castrated 30% male and 70% female. |
| Supplier: | Commercial farm, Montérégie, Québec, Canada |
| Age when tested: | The test article was intended for administration of test strain of piglets from approximately 17 days of age. |
| Weight range at study initiation: | 3.120-7.295 Kg |
| Acclimatisation: | 1 day |
| Medication: | No concurrent medication or vaccination was administered within 3 days prior to and during the study to any of the study animals |

The following Table 7 generally summarizes the study design:

| Day of activity | T1 | T2 |
| --- | --- | --- |
| Day −2 | Arrival of RF18+ pigs in the isolation facilities and random allocation of pigs, general health control and weight | |
| Day 0 (approx. 17 days of age) | non-pathogenic F18 administration | Placebo |
| Days 1-11 | Daily health control | |
| Day 11-12-13 | Challenge with F8-STEC | |
| Day 11 to 18 | Observations for health | |
| Day 18 | Necropsy and microbiology | |

II—Procedure and Evaluation

T1 group and T2 group animals could not be commingled due to the nature of the tested product (i.e., a live vaccine) requiring treated animals to be housed separately from placebo controls. The non-pathogenic F18 strain and placebo solutions were prepared by persons not involved in the animal phase. A code "A" and "B" was randomly assigned to the non-pathogenic F18 strain and placebo solutions. Rooms were randomly allocated to treatment and identified as rooms 1 and 2. Each room had all T1 group or all T2 group animals commingled in a single pen. The personnel involved in the animal phase and doing laboratory analysis were blinded to treatment and room allocations. For the necropsy phase, the sequence of animals to be necropsied was randomly assigned and animals were re-identified as A to AD. The person performing the necropsy was blinded to pig identification and treatment. The randomization codes were kept in a sealed envelope by the biostatistician in charge.

a) Preparation of the Non-Pathogenic F18 Strain and Administration

The non-pathogenic F18 strain was cultured in a fermenter, then the bacteria was frozen and stored at −78° C. in 10 mL glass vials containing 200 nominal doses. The frozen bacteria were diluted with water at room temperature prior to use.

The dose was administered once at one day post-weaning (Day 0) at approximately $3 \times 10^8$ CFU per 2-mL dose. The dose was administered orally using a syringe mounted with a rubber tube. The control animals received the same amount of placebo solution (water).

b) Challenge Strain (F18-STEC Strain EcL 14724)

The challenge strain used in this assay was re-isolated from a piglet (#381) previously challenged with the EcL 14724 strain (positive for Stx2, F18ab, AIDA and Paa). The challenge strain was orally administered once at the 3 consecutive days 11, 12 and 13 of the study at approximately $1 \times 10^{10}$ CFU per pig. Each challenge dose was administered using a gelatin capsule as a replacement for oesophagic intubation. Carbadox (an antibiotic stimulating the release of the shigatoxin) was orally administered in a gelatin capsule immediately after administration of the challenge strain to trigger the release of the Shigatoxin.

c) General Health Evaluation

Pigs were observed once daily prior to the challenge period for general health. Following the first challenge, animals were monitored twice daily for general health, including depression, dehydration, appetite and for any clinical signs associated to edema disease: ataxia, facial or limb edema, sudden death.

d) Evaluation of the Shedding of the Challenge Strain

Fecal shedding of the challenge strain was quantified using a Most-Probable-Number PCR (MPN-PCR) method targeting the gene coding for the FedA major protein of the F18 fimbriae.

e) Necropsy

Necropsies were carried out at 7 days post-first challenge. Colonization of the caecum by the challenge strain was quantified using a Most-Probable-Number PCR method targeting the gene coding for the FedA major protein of the F18 fimbriae using approximately 2 cm$^2$ portion of the tissue.

III—Results

PCR analysis demonstrated the efficacy of the administration of the non-pathogenic F18 strain to prevent excretion of the challenge F18 shigatoxigenic pathogenic strain. A reduction of about 2.5 log of fecal shedding was observed for the treated animals compared to the placebo animals at 4 days post-last challenge (Table 8). At 4 days post last challenge, 93% of placebo animals shed more than $1\times10^5$ CFU of the challenge strain per gram of fecal sample while only 42% of treated animals did (Table 9).

The following Table 8 shows shedding of the challenge strain at day 4 post-last challenge:

|  | Median of shedding (CFU of the challenge strain/g of fecal sample) |
| --- | --- |
| Placebos animals | $7.8 \times 10^6$ |
| Treated animals | $5.2 \times 10^4$ |

The following Table 9 shows the proportion of pigs shedding the challenge strain at different bacterial load at day 4 post-last challenge:

| | CFU of the challenge strain/g of fecal samples | | | |
| --- | --- | --- | --- | --- |
| | $<1 \times 10^4$ | $10^4$ | $10^5$ | $>1 \times 10^6$ |
| Placebo animals | 0% | 7% | 33% | 60% |
| Treated animals | 25% | 33% | 17% | 25% |

A reduction of about 1 log of the challenge strain detected in the caecum was observed for the treated animals (administered the non-pathogenic F18 strain) compared to the placebo animals at 5 days post-last challenge (Table 10). At 5 days post-last challenge, more than 53% of placebo animals shed more than $1\times10^5$ CFU of the challenge strain per gram of caecum tissue while only 8% of treated animals did (Table 11). More than 80% of placebo animals were colonized in the caecum by more than $1\times10^4$ CFU of the challenge strain per gram of caecum compared to 50% of treated animals at 5 days post-last challenge (Table 11).

The following Table 10 shows colonization of the caecum by the challenge strain at day 5 post-last challenge:

|  | Median of caecum colonization (CFU of the challenge strain/g of caecum tissue) |
| --- | --- |
| Placebo animals | $3.4 \times 10^5$ |
| Treated animals | $1.5 \times 10^4$ |

The following Table 11 shows the proportion of pigs of which the caecum was colonized by the challenge strain at different bacterial load at day 5 post-last challenge:

| | CFU of the challenge strain/g of caecum samples | | | |
| --- | --- | --- | --- | --- |
| | $<1 \times 10^2$ | $10^2$ | $10^3$ | $10^4$ | $>1 \times 10^5$ |
| Placebo animals | 7% | 7% | 7% | 27% | 53% |
| Treated animals | 8% | 17% | 25% | 42% | 8% |

Based on the resulting reduction of the challenge strain colonization and reduction of excretion, this study suggests that intestinal delivery of a composition including the non-pathogenic F18 strain is capable of preventing F18 *E. coli* edema-causing intestinal bacterial infection.

The following clauses provide a further description of examples of non-limiting embodiments in accordance with the present invention:

Clauses

Clause 1: Isolated *E. coli* strain deposited at the International Depositary Authority of Canada (IDAC) on Jun. 20, 2013 and attributed accession number 200613-01.

Clause 2: The isolated *E. coli* strain of clause 1, in lyophilized form.

Clause 3: The isolated *E. coli* strain of clause 1, in frozen form.

Clause 4: The isolated *E. coli* strain of clause 1, wherein the strain is in association with a feed acceptable carrier.

Clause 5: A composition comprising the isolated *E. coli* strain of any one of clauses 1 to 3 and a feed acceptable carrier.

Clause 6: The composition of clause 5, further comprising an isolated live non-pathogenic *E. coli* that expresses the F4 fimbriae.

Clause 7: The composition of clause 6, wherein said non-pathogenic *E. coli* that expresses the F4 fimbriae is the strain deposited at the International Depositary Authority of Canada on Jan. 21, 2005 and attributed accession number IDAC 210105-01.

Clause 8: A method for preventing F18 pathogenic *E. coli* intestinal infection in an animal, comprising intestinal delivery to the animal of an effective amount of a live *E. coli* strain deposited at the International Depositary Authority of Canada (IDAC) on Jun. 20, 2013 and attributed accession number 200613-01

Clause 9: The method of clause 8, wherein said intestinal delivery is obtained by oral administration of the live *E. coli* strain.

Clause 10: The method of clause 8 or 9, wherein said live *E. coli* strain is in lyophilized form.

Clause 11: The method of clause 8 or 9, wherein said live *E. coli* strain is in frozen form.

Clause 12: The method of clause 8 or 9, wherein said live *E. coli* strain is in association with a feed acceptable carrier.

Clause 13: The method according to any one of clauses 8 to 12, wherein said effective amount is of at least $5\times10^7$ CFU.

Clause 14: A method according to any one of clauses 8 to 12, wherein said animal is a pig.

Clause 15: A method for preventing edema disease or diarrhea caused by an F18 pathogenic *E. coli* infection in an animal, comprising intestinal delivery to the animal of a live *E. coli* strain deposited at the International Depositary Authority of Canada (IDAC) on Jun. 20, 2013 and attributed accession number 200613-01.

Clause 16: The method of clause 15, wherein said intestinal delivery is obtained by oral administration of the live *E. coli* strain.

Clause 17: The method of clause 15 or 16, wherein said live *E. coli* strain is in lyophilized form.

Clause 18: The method of clause 15 or 16, wherein said live *E. coli* strain is in frozen form.

Clause 19: The method of clause 15 or 16, wherein said live *E. coli* strain is in association with a feed acceptable carrier.

Clause 20: The method according to any one of clauses 15 to 19, wherein said effective amount is of at least $5 \times 10^7$ CFU.

Clause 21: A method according to any one of clauses 15 to 20, wherein said animal is a pig.

Clause 22: Use, for preventing an F18 pathogenic *E. coli* intestinal infection in an animal, of an effective amount of an effective amount of a live *E. coli* strain deposited at the International Depositary Authority of Canada (IDAC) on Jun. 20, 2013 and attributed accession number 200613-01, the strain being adapted for intestinal delivery in the animal.

Clause 23: Use, in the manufacture of a composition for use in preventing an F18 pathogenic *E. coli* intestinal infection in an animal, of an effective amount of a live *E. coli* strain deposited at the International Depositary Authority of Canada (IDAC) on Jun. 20, 2013 and attributed accession number 200613-01, the composition being adapted for intestinal delivery in the animal.

Clause 24: Use, for preventing edema disease or diarrhea caused by an F18 pathogenic *E. coli* infection in an animal, of an effective amount of an effective amount of a live *E. coli* strain deposited at the International Depositary Authority of Canada (IDAC) on Jun. 20, 2013 and attributed accession number 200613-01, the strain being adapted for intestinal delivery in an animal.

Clause 25: Use, in the manufacture of a composition for use in preventing edema disease or diarrhea caused by an F18 pathogenic *E. coli* infection in an animal, of an effective amount of an effective amount of a live *E. coli* strain deposited at the International Depositary Authority of Canada (IDAC) on Jun. 20, 2013 and attributed accession number 200613-01, the composition being adapted for intestinal delivery in an animal.

Clause 26: The use of any one of clauses 22 to 25, wherein said live *E. coli* strain is adapted for oral administration.

Clause 27: The use of any one of clauses 22 to 26, wherein said live *E. coli* strain is in lyophilized form.

Clause 28: The use of any one of clauses 22 to 26, wherein said live *E. coli* strain is in frozen form.

Clause 29: The use of any one of clauses 22 to 26, wherein said live *E. coli* strain is in association with a feed acceptable carrier.

Clause 30: The use according to any one of clauses 22 to 29, wherein said effective amount is of at least about $5 \times 10^7$ CFU.

Clause 31: The use according to any one of clauses 22 to 30, wherein said animal is a pig.

Clause 32: The isolated *E. coli* strain of any one of clauses 1 to 4, for use in preventing an F18 pathogenic *E. coli* intestinal infection in an animal, the strain being adapted for intestinal delivery in the animal.

Clause 33: The isolated *E. coli* strain of any one of clauses 1 to 4, for use in the manufacture of a composition for use in preventing an F18 pathogenic *E. coli* intestinal infection in an animal, the composition being adapted for intestinal delivery in the animal.

Clause 34: The isolated *E. coli* strain of any one of clauses 1 to 4, for use in preventing edema disease or diarrhea caused by an F18 pathogenic *E. coli* infection in an animal, the strain being adapted for intestinal delivery in the animal.

Clause 35: The isolated *E. coli* strain of any one of clauses 1 to 4, for use in the manufacture of a composition for use in preventing edema disease or diarrhea caused by an F18 pathogenic *E. coli* infection in an animal, the composition being adapted for intestinal delivery in the animal.

Note that titles or subtitles may be throughout the present for convenience of a reader, which in no way should limit the scope of the invention. Moreover, certain theories are proposed and disclosed herein; however, in no way they, whether they are right or wrong, should limit the scope of the invention so long as the invention is practiced according to the present disclosure without regard for any particular theory or scheme of action.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

While the herein described studies have used weaned pigs, the person of skill will readily understand that the pigs being treated may alternatively be pre-weaning pigs.

As used herein, "around", "about" or "approximately" shall generally mean within 20 percent, preferably within 10 percent, and more preferably within 5 percent of a given value or range. Numerical quantities given herein are generally approximate; meaning that the term "around", "about" or "approximately" can be inferred if not expressly stated.

All references cited throughout the specification are hereby incorporated by reference in their entirety.

The scope of the claims should not be limited by the preferred embodiments set forth in the examples, but should be given the broadest interpretation consistent with the description as a whole.

The invention claimed is:

1. A method for preventing an F18 pathogenic *E. coli* intestinal infection in an animal, comprising intestinal delivery to the animal of an effective amount of a live *E. coli* strain deposited at the International Depositary Authority of Canada (IDAC) on Jun. 20, 2013 and attributed accession number 200613-01.

2. The method of claim 1, wherein said intestinal delivery is obtained by oral administration of the live *E. coli* strain.

3. The method of claim 2, wherein said live *E. coli* strain is in lyophilized form.

4. The method of claim 2, wherein said live *E. coli* strain is in frozen form.

5. The method of claim 2, wherein said live *E. coli* strain is in association with a feed acceptable carrier.

6. The method according to claim 2, wherein said animal is a pig.

7. A method for preventing edema disease or diarrhea caused by an F18 pathogenic *E. coli* infection in an animal, comprising intestinal delivery to the animal of an effective amount of a live *E. coli* strain deposited at the International Depositary Authority of Canada (IDAC) on Jun. 20, 2013 and attributed accession number 200613-01.

8. The method of claim 7, wherein said intestinal delivery is obtained by oral administration of the live *E. coli* strain.

9. The method of claim 8, wherein said live *E. coli* strain is in lyophilized form.

10. The method of claim 8, wherein said live *E. coli* strain is in frozen form.

11. The method of claim 8, wherein said live *E. coli* strain is in association with a feed acceptable carrier.

12. A method according to claim 8, wherein said animal is a pig.

13. The method according to claim 1, wherein said amount is within the range of about $5 \times 10^6$ to about $3 \times 10^{10}$ CFU per animal.

14. The method according to claim 1, wherein said amount is of at least $5 \times 10^7$ CFU per animal.

15. The method according to claim 7, wherein said amount is within the range of about $5 \times 10^6$ to about $3 \times 10^{10}$ CFU per animal.

16. The method according to claim 7, wherein said amount is of at least $5 \times 10^7$ CFU per animal.

17. The method according to claim 7, for preventing edema disease caused by an F18 pathogenic *E. coli* infection in an animal.

18. The method according to claim 7, for preventing diarrhea caused by an F18 pathogenic *E. coli* infection in an animal.

* * * * *